US010040038B2

(12) United States Patent
Dehan et al.

(10) Patent No.: US 10,040,038 B2
(45) Date of Patent: Aug. 7, 2018

(54) DEVICE FOR MIXING AT LEAST TWO CONSTITUENTS

(75) Inventors: Christophe F. Dehan, Saint Ismier (FR); Didier Lamy, Poisy (FR)

(73) Assignee: EVEON, Montbonnot, Saint Martin (FR)

( * ) Notice: Subject to any disclaimer, the term of this patent is extended or adjusted under 35 U.S.C. 154(b) by 1019 days.

(21) Appl. No.: 13/996,053

(22) PCT Filed: Dec. 19, 2011

(86) PCT No.: PCT/FR2011/053054
§ 371 (c)(1),
(2), (4) Date: Jun. 20, 2013

(87) PCT Pub. No.: WO2012/085428
PCT Pub. Date: Jun. 28, 2012

(65) Prior Publication Data
US 2013/0274656 A1 Oct. 17, 2013

(30) Foreign Application Priority Data
Dec. 24, 2010 (FR) ...................................... 10 61242

(51) Int. Cl.
*B01F 5/06* (2006.01)
*A61M 5/168* (2006.01)
(Continued)

(52) U.S. Cl.
CPC ........... *B01F 5/06* (2013.01); *A61M 5/16827* (2013.01); *A61M 5/19* (2013.01); *A61M 5/20* (2013.01);
(Continued)

(58) Field of Classification Search
CPC .... B01F 5/06; B01F 13/1055; B01F 15/0237; B01F 13/002; B01F 15/0217;
(Continued)

(56) References Cited

U.S. PATENT DOCUMENTS 5,466,220 A * 11/1995 Brenneman ........... A61J 1/2089
604/411
2002/0045856 A1 * 4/2002 Jaafar ................. A61M 5/1407
604/113
(Continued)

FOREIGN PATENT DOCUMENTS

CN 1193919 A 9/1998
CN 1011460216 A 6/2009
(Continued)

*Primary Examiner* — Bhisma Mehta
*Assistant Examiner* — Hamza Darb
(74) *Attorney, Agent, or Firm* — Ware, Fressola, Maguire & Barber LLP

(57) ABSTRACT

The apparatus (1) is designed to mix at least two ingredients coming from at least two distinct reservoirs (2, 3). It has at least two distinct orifices (6, 7) suitable for being connected to the reservoirs (2, 3), a motor-driven pump (15), a fluid-connection selector (9) including at least one network of through channels (12) suitable for putting at least one of the orifices into communication with the pump (15), the fluid-connection selector (9) being arranged to be movable between a plurality of positions in order to make it possible, selectively and by means of the pump (15), to transfer at least one ingredient from one orifice to the other orifice or towards the pump (15) and to blend the resulting mixture.

11 Claims, 10 Drawing Sheets

(51) Int. Cl.
  *B01F 13/00* (2006.01)
  *B01F 13/10* (2006.01)
  *B01F 15/02* (2006.01)
  *A61M 5/20* (2006.01)
  *A61M 5/19* (2006.01)
  *A61M 5/162* (2006.01)
  *A61M 39/22* (2006.01)
  *A61J 3/00* (2006.01)

(52) U.S. Cl.
  CPC ........... *A61M 5/204* (2013.01); *B01F 13/002* (2013.01); *B01F 13/1055* (2013.01); *B01F 15/0217* (2013.01); *B01F 15/0237* (2013.01); *A61J 3/002* (2013.01); *A61M 5/162* (2013.01); *A61M 5/2066* (2013.01); *A61M 2005/206* (2013.01); *A61M 2039/224* (2013.01); *A61M 2205/502* (2013.01); *B01F 2215/0034* (2013.01)

(58) Field of Classification Search
  CPC .... B01F 2215/0034; A61M 5/19; A61M 5/20; A61M 5/204; A61M 5/16827; A61M 2205/502; A61M 2005/206; A61M 5/2066; A61M 5/162; A61M 2039/224; A61J 3/002
  See application file for complete search history.

(56) References Cited

U.S. PATENT DOCUMENTS

| | | | |
|---|---|---|---|
| 2002/0112530 | A1 | 8/2002 | Kitagawa |
| 2005/0284886 | A1* | 12/2005 | Penciu ................ B01F 13/1058 222/145.6 |
| 2007/0106210 | A1* | 5/2007 | Fischer .................... A61C 5/62 604/82 |
| 2008/0300483 | A1* | 12/2008 | Nemoto ................ A61M 5/007 600/431 |
| 2012/0029464 | A1* | 2/2012 | Kragelund ............ A61J 1/2089 604/414 |

FOREIGN PATENT DOCUMENTS

| | | |
|---|---|---|
| DE | 44 44 987 A1 | 5/1995 |
| EP | 0 013 334 A2 | 7/1980 |
| FR | 2 708 204 A1 | 2/1995 |
| FR | 2708204 A1 | 2/1995 |
| JP | S58169452 A | 10/1983 |
| JP | H09173447 A | 7/1997 |
| JP | 2002537950 A | 11/2002 |
| JP | 2005319390 A | 11/2005 |
| JP | 2009534144 A | 9/2009 |
| JP | 201211295 A | 1/2012 |
| JP | 5588768 B2 | 9/2014 |

* cited by examiner

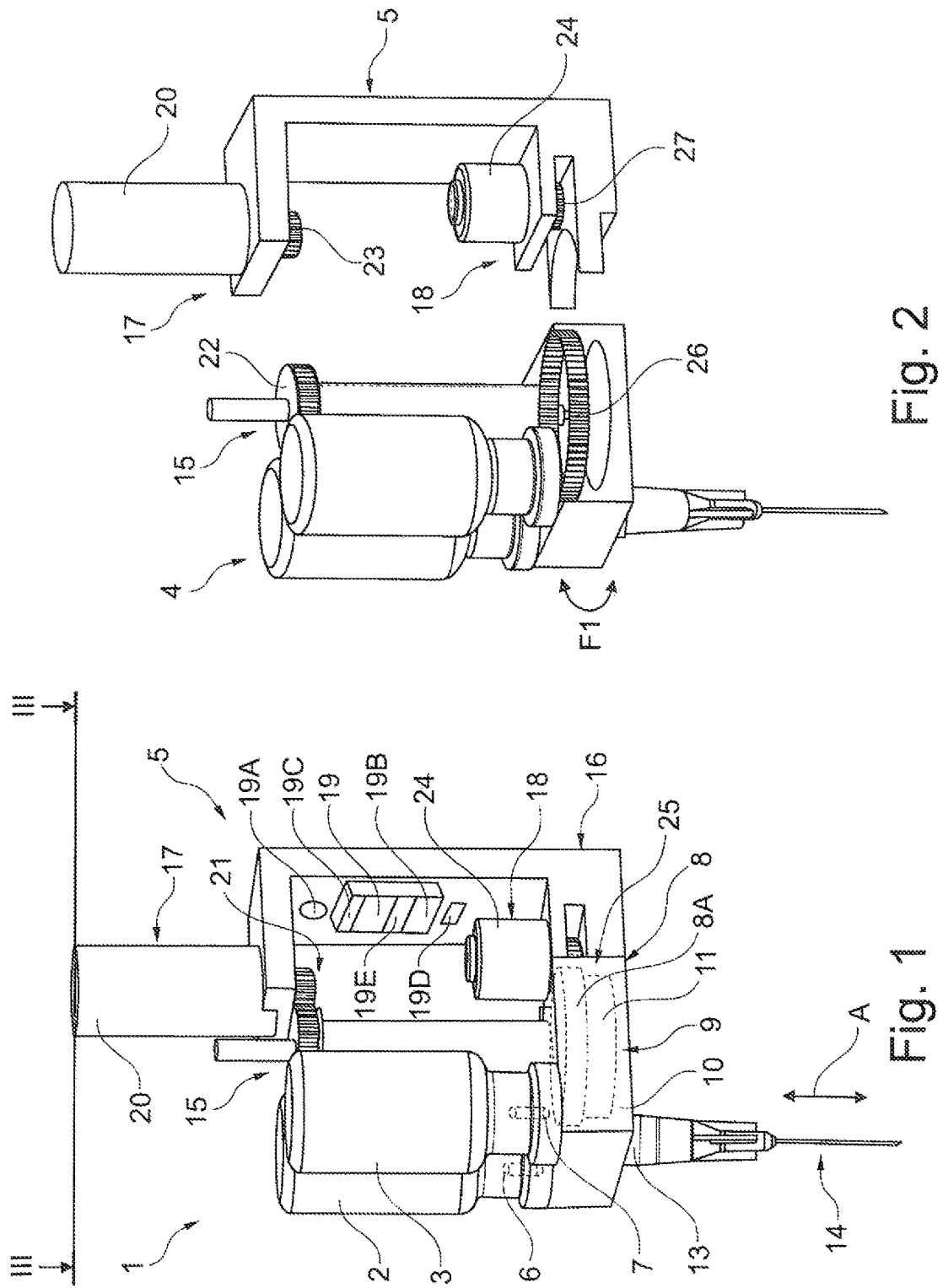

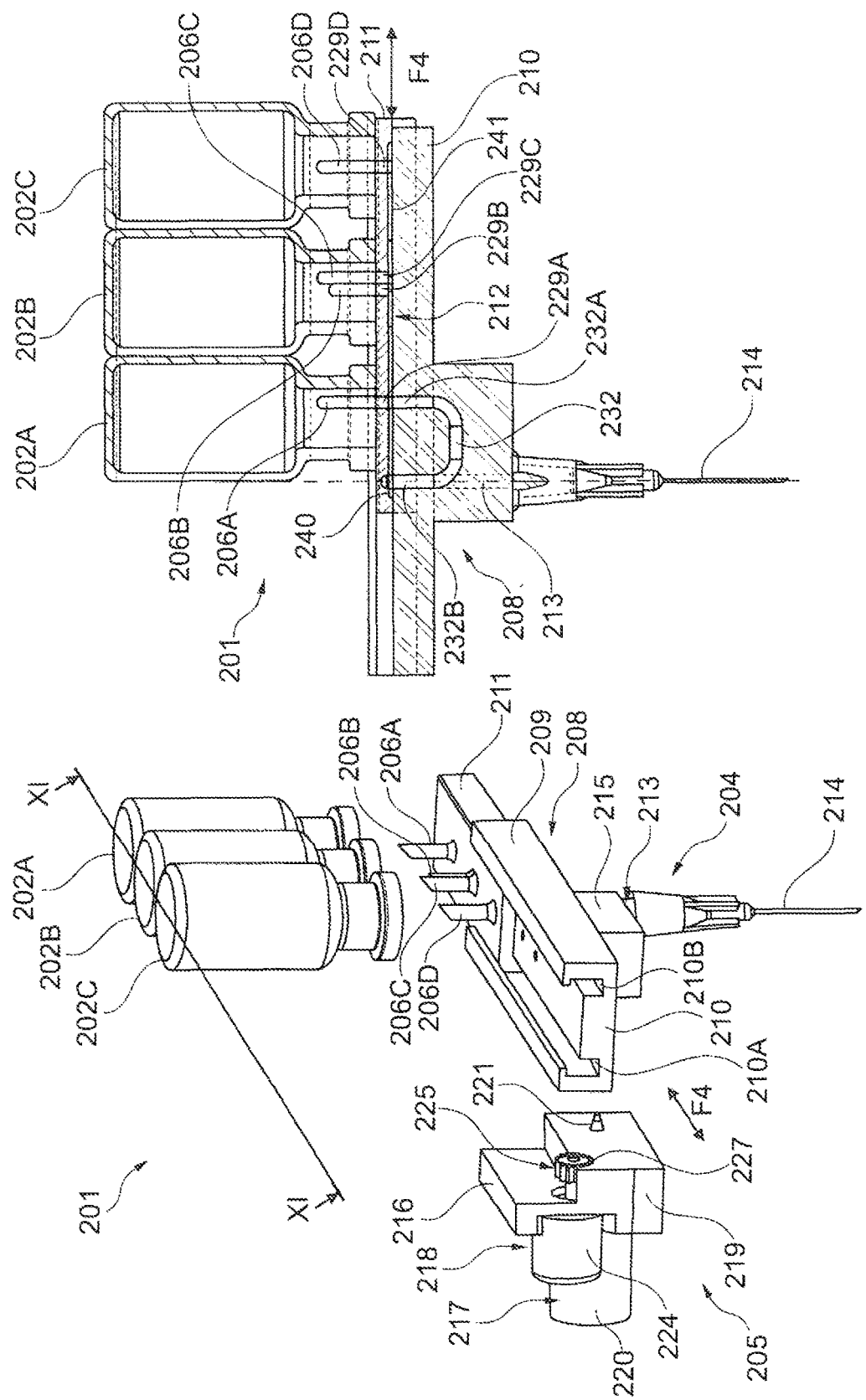

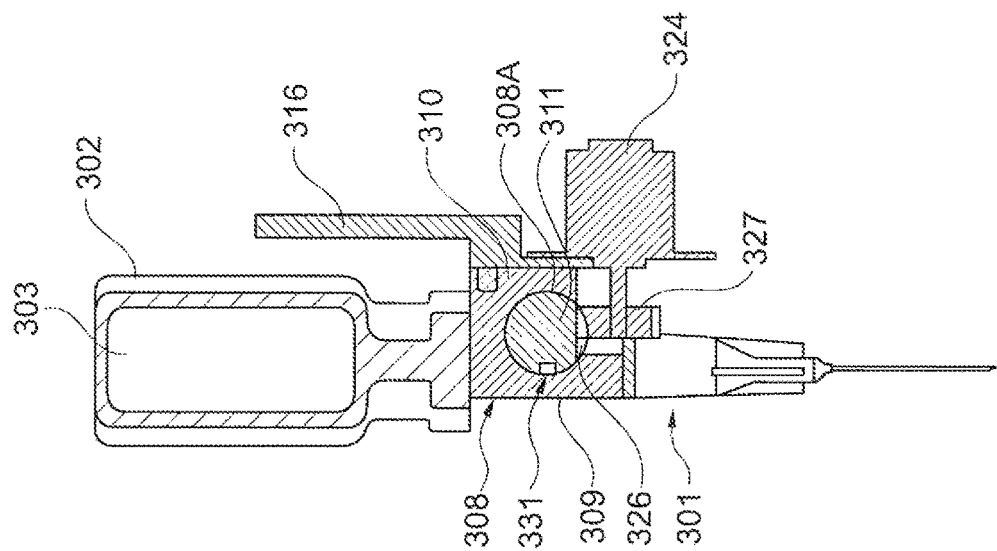
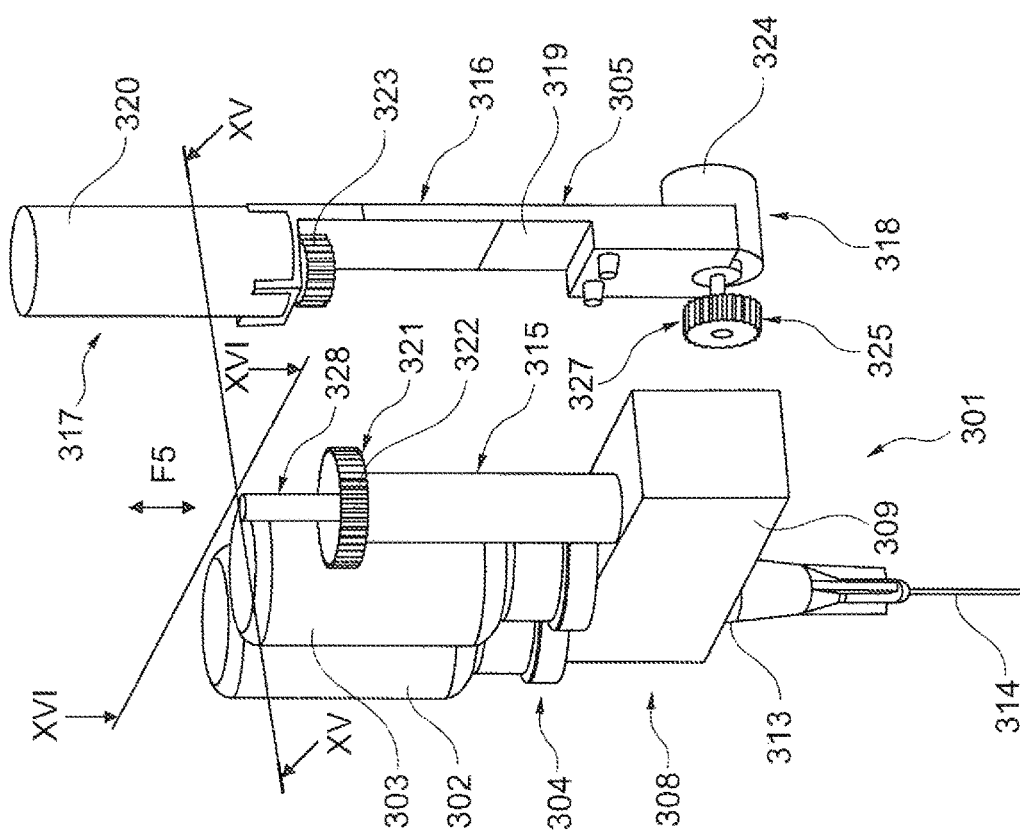
Fig. 15
Fig. 14

DEVICE FOR MIXING AT LEAST TWO CONSTITUENTS

CROSS REFERENCE TO RELATED APPLICATIONS

This application is the U.S. National Stage of International Application Number PCT/FR2011/053054 filed on Dec. 19, 2011 which application claims priority under 35 USC § 119 to French Patent Application No. 1061242 filed on Dec. 24, 2010, which applications are hereby incorporated by reference in their entirety.

TECHNICAL FIELD

The invention relates to mixing apparatus for mixing at least two ingredients coming from at least a first reservoir and a second reservoir distinct from the first reservoir, said mixing apparatus having at least one first orifice suitable for being connected to the first reservoir, and at least one second orifice distinct from the first orifice and suitable for being connected to the second reservoir, and a motor-driven pump. Such mixing apparatus makes it possible to obtain a homogeneous mixture.

The invention also relates to medical-use miniaturized injection apparatus including such mixing apparatus.

PRIOR ART

Many mixtures of ingredients, e.g. for therapeutic purposes in the medical or animal fields, or for other purposes in the cosmetics field, are unstable in the state in which they are ready to be administered. Therefore, the various ingredients of such mixtures are kept in the separated state in various bottles or other containers and they are mixed immediately before administering by the user. For example, a first ingredient is often in the form of a solid powder or of a dehydrated lyophilized (freeze-dried) substance to be made up with a second ingredient of the solvent type, or indeed said first ingredient is in the form of a concentrate having high viscosity to be diluted by a solvent, requiring an appropriate making-up or mixing protocol in order to obtain a homogeneous solution.

"Administering" means any act making it possible to have an ingredient absorbed by a user, be it by injection, perfusion, oral route, cutaneous route, or by any other means.

Conventionally, in the range five to ten manual steps are necessary in order to obtain the mixture of the ingredients, involving syringes and bottles or other containers, namely: taking an ingredient from one of the bottles or other containers with a syringe; transferring it to another bottle or container containing the second ingredient, while avoiding emulsion or clumping effects; blending the mixture in order to obtain a homogeneous solution of the two ingredients; taking the final solution with a syringe; and administering it to the patient.

Apparatus as described above is known, for example, from Patent Document FR-2 708 204. That apparatus includes a syringe body equipped with a piston that is pre-filled with a liquid first ingredient. That apparatus is provided with means for fastening the syringe body to a standard medical bottle or other container filled with the second ingredient. In order to mix the two ingredients, the syringe body is fastened to the bottle or other container, and the liquid ingredient is injected manually into the bottle or other container by means of the piston. A drawback with that apparatus is that it requires pre-filling of the syringe, which is less practical and more expensive than using standard bottles or other containers.

In general, all of the steps of obtaining the mixture and of blending it require from three to eight sterile consumables (syringes, needles, etc.) to be used in order to satisfy appropriate hygiene conditions. In addition, repeated use of syringes with needles increases the risks of injury from the needles. Finally, those steps are also accompanied by waiting times. That is why administering such mixtures of ingredients requires assistance from a medical professional or requires the user to be trained.

Currently, about 50% of the new therapeutic molecules that are being developed are of biological origin, preservable mainly in solid powder form or in lyophilized form, to be made up immediately before administering.

In addition, it is essential to guarantee the safety of the people performing the mixing, and in particular when the mixing involves cytotoxic substances. In order to guarantee safety, certain air extraction installations are sometimes used. Such installations represent a non-negligible additional cost and can be used only in specific dedicated places, which does not make it possible for them to be used in the majority of situations of use. Thus, it is necessary to propose mixing apparatus of the "closed" type, making it possible for mixing to take place without any risk of contamination from the liquid, powder, or vapor, and making it possible to guarantee a good level of asepsis.

There is thus a genuine need for medical apparatus making it possible to mix ingredients in a manner that is simple, safe, and user-independent, and optionally making it possible to administer such mixtures.

SUMMARY OF THE INVENTION

An object of the invention is to satisfy this need while also mitigating the drawbacks of existing apparatus by proposing mixing apparatus making it possible to mix two ingredients that is very simple to handle and that can be used by any non-medically-trained user, and optionally incorporated into medical-use miniaturized injection apparatus. An object of the invention is also to propose mixing apparatus that makes it possible to obtain a homogeneous mixture. This offers multiple advantages:

limiting the risk of injury from the sharp articles (needles) that are commonly used;
limiting the handling time (automation, making-up, without intervention from the operator); and
low exposure or no exposure to handled active molecules that can be dangerous for an operator who is not the patient.

To this end, the invention provides mixing apparatus for mixing at least two ingredients coming from at least a first reservoir and a second reservoir distinct from the first reservoir, the mixing apparatus having at least one first orifice suitable for being connected to the first reservoir, and at least one second orifice distinct from the first orifice and suitable for being connected to the second reservoir, and a motor-driven pump, said mixing apparatus being characterized in that it includes a fluid-connection selector connected to the pump and including a network of channels, the fluid-connection selector being provided with at least:

a stationary portion including at least a portion of the network of channels opening out at least via the first orifice and via the second orifice;

a moving portion including at least one other portion of the network of channels and mounted to move between a plurality of positions including at least:
a first position in which the network of channels puts the at least one first orifice and the at least one second orifice into communication with the pump so as to make it possible, by means of the pump, to transfer at least one ingredient from the first orifice towards the second orifice via the pump; and
a second position in which the network of channels puts the second orifice into communication with the pump so as to make it possible, by means of the pump, to blend the resulting mixture by causing it to flow through the network of channels.

The term "motor-driven" pump means a pump provided with means serving to transform any energy, e.g. electrical energy, into mechanical energy. In accordance with this definition, a diaphragm pump, in particular, is a motor-driven pump.

With the mixing apparatus of the invention, mixing (or making-up) and blending of the ingredients is facilitated: after two reservoirs containing respective ones of the two ingredients are fastened to the mixing apparatus, the fluid-connection selector is adjusted to interconnect the orifices leading to the reservoirs, and then the motor-driven pump is actuated to cause the ingredients to flow from one reservoir to the other so as to mix them, and then to blend the mixture in a reservoir.

These very simple operations can be performed directly by the user, even if the user is not trained in medical techniques. In addition, since mixing and blending are automated, the risks of error are reduced. In addition, standard bottles or other containers may be used directly as reservoirs and the number of sterile consumables necessary is small. Finally, since the mixture flows through the network of channels before it is used, the accuracy of metering or "dosage" between the various ingredients is guaranteed.

Mixing apparatus of the invention may advantageously have the following features:
the pump is at least suitable for being coupled to a pump reservoir;
the mixing apparatus may be provided with two second orifices suitable for being coupled to the second reservoir so that, in the second position, the blending is obtained by the pump causing said mixture to flow between said second orifices;
the network of channels of the fluid-connection selector includes at least one outlet channel for discharging the mixture from said apparatus, it being possible for the moving portion of the fluid-connection selector to take up a third position in which said network of channels puts the pump or the second orifice into communication with the outlet channel in order to discharge the mixture from the mixing apparatus;
the mixing apparatus may have at least one third orifice suitable for being connected to a third reservoir distinct from the first and second reservoirs, the moving portion of the fluid-connection selector being suitable for being in a third position in which the network of channels puts the second orifice and the third orifice into communication with each other in order to enable the mixture to be transferred from the second orifice towards the third orifice;
at least one of the first orifice(s), of said second orifice(s), and of the third orifice(s) is formed individually on an end-piece, and, when the mixing apparatus has two second orifices, the end-pieces carrying the two second orifices have different lengths, making it possible to improve the flow of fluid through the second reservoir;
at least one of the first orifice(s), of the second orifice(s), and of the third orifice(s) is formed individually on an end-piece, and, when the mixing apparatus has two second orifices, the two second orifices have mutually different inside end section dimensions, making it possible to improve the flow of fluid through the second reservoir;
the fluid-connection selector is arranged to be coupled to a motor drive suitable for moving it between the first, second, and third positions;
the mixing apparatus may include a disposable first assembly including the fluid-connection selector, and a reusable second assembly, including the motor drive of the pump and of the fluid-connection selector, the disposable first assembly and the reusable second assembly being arranged to be connectable and detachable respectively one relative to the other;
the disposable first assembly includes at least said first reservoir containing a solvent and the second reservoir containing a solid powder or a lyophilized substance;
the moving portion of the fluid-connection selector is arranged to be movable in rotation relative to the stationary portion; and
the moving portion of the fluid-connection selector is arranged to be movable in translation relative to the stationary portion.

The invention also provides medical-use miniaturized injection apparatus, characterized in that it includes mixing apparatus as defined above, and a needle connected to said fluid-connection selector.

In the medical-use miniaturized injection apparatus of the invention, the needle may be advantageously mounted to move in an enclosure of said injection apparatus.

BRIEF DESCRIPTION OF THE DRAWINGS

The present invention can be better understood and other advantages appear on reading the following detailed description of embodiments given by way of non-limiting example and with reference to the accompanying drawings, in which:

FIG. 1 is a diagrammatic perspective view of a first embodiment of the mixing apparatus of the invention;

FIG. 2 is an exploded perspective view of the mixing apparatus of FIG. 1;

FIG. 10 is an exploded perspective view of a third embodiment of the mixing apparatus of the invention;

FIG. 11 is a section view on a vertical plane containing the axis XI-XI of FIG. 10, showing the mixing apparatus of FIG. 10;

FIG. 14 is an exploded perspective view of a fourth embodiment of the mixing apparatus of the invention;

FIG. 15 is a section view on a vertical plane containing the axis XV-XV of FIG. 14, showing the mixing apparatus of FIG. 14;

DESCRIPTION OF EMBODIMENTS

Figure 3:
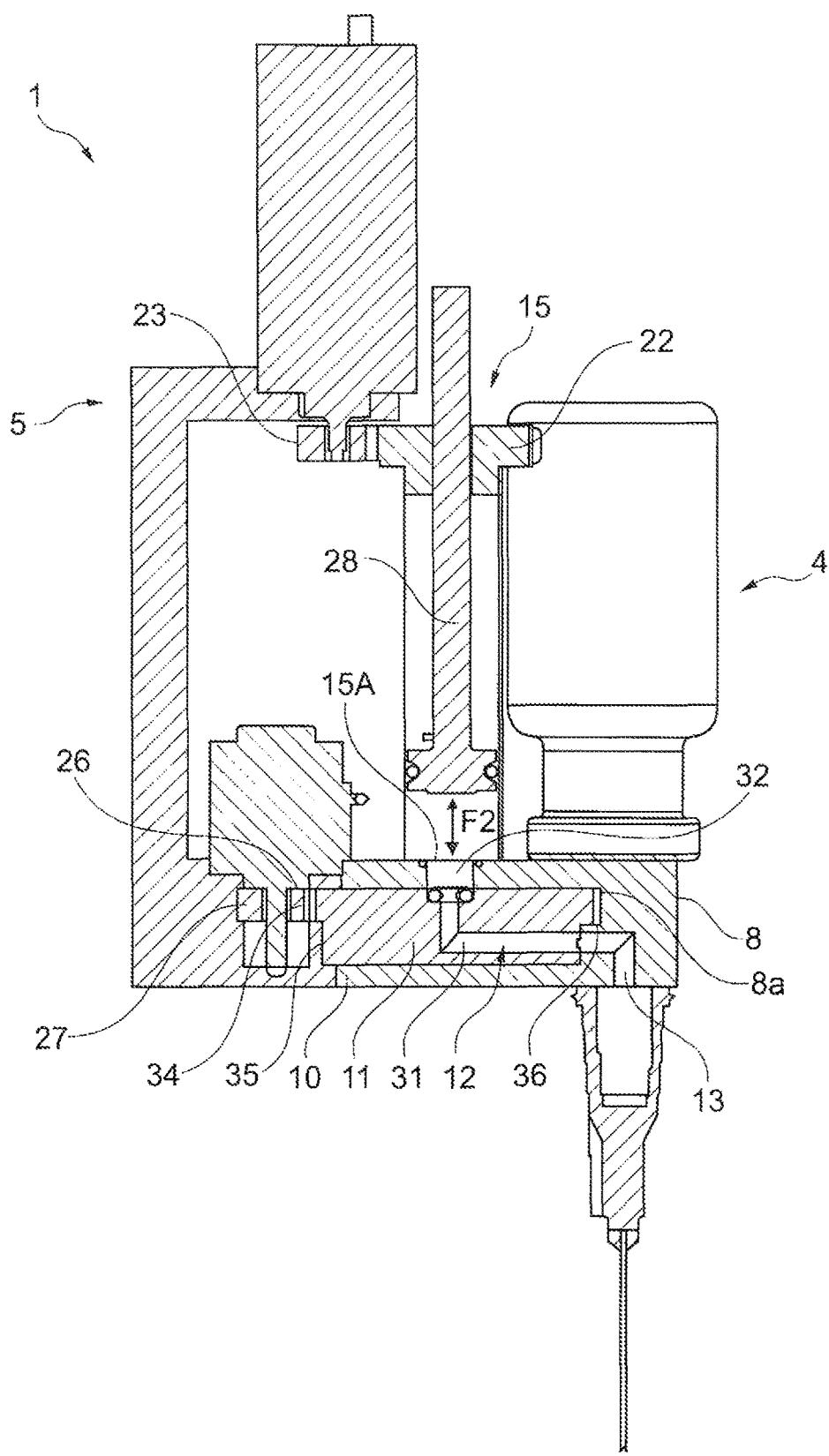
FIG. 3 is a section view on a vertical plane containing the axis III-III of FIG. 1, showing the mixing apparatus of FIG. 1.

FIG. 1 shows medical-use miniaturized mixing apparatus 1 of the invention making it possible to mix two ingredients contained respectively in a first reservoir 3 and in a second reservoir 2. Preferably, standard medical bottles or other containers are used as first and second reservoirs 3, 2, such bottles or other containers commonly also being referred to as "vials", "cartridges", or "pouches".

On a stand 8, the mixing apparatus 1 firstly includes two end-pieces provided respectively with a first orifice 7 and with a second orifice 6, and suitable for receiving respectively a first reservoir 3 and a second reservoir 2 in sealed manner so as to preserve the original sterility of the first and second reservoirs 3, 2, and secondly includes an outlet channel 13 for discharging the mixture, via an injection needle 14 in this example.

Preferably, the mixing apparatus 1 is advantageously inserted into medical-use miniaturized injection apparatus having an enclosure (not shown), and the needle 14 is mounted to move in said enclosure in an axial direction indicated by arrow A in FIG. 1, the needle being moved by movement means 14A adapted to move the needle 14 into a projecting position in which it projects out of the enclosure in order to inject the mixture. Preferably, the movement means 14A are motor-driven.

The stand 8 forms a stationary portion 10 of a rotary fluid-connection selector 9 and is provided with a substantially semicircular recess 8A (shown in detail in FIG. 5) for receiving a substantially circular moving portion 11 of the fluid-connection selector 9. As described below in particular with reference to FIGS. 4 to 6, the fluid-connection selector 9 has a network of channels 12 in its stationary portion 10 and in its moving portion 11, it being possible for the network portions in stationary portion 10 and the network portions in the moving portion 11 to be put into register with each other so as to connect the end-pieces provided with first and second orifices 7, 6 selectively to the outlet channel 13. Preferably, the fluid-connection selector 9 may be implemented using simple plastics parts, in a manner known per se.

It should be noted that the end-pieces provided with first and second orifices 7, 6 are preferably equipped with piercing means (not shown) for piercing stoppers of the first and second reservoirs 3, 2, and with sealing gaskets for sealing the connections between the first and second reservoirs 3, 2 and the network of channels 12 of the fluid-connection selector 9.

The mixing apparatus 1 also includes a motor-driven pump 15 mounted on the stand 8. In this example, this pump is of the two-directional piston pump type having a single port 15A visible in FIG. 3, and adapted to cause the ingredients to flow through the network of channels 12 of the fluid-connection selector 9, between the end-pieces provided with first and second orifices 7, 6 and the outlet channel 13.

As can also be seen in FIG. 1, the mixing apparatus 1 further includes, on a frame 16, a first motor drive 17 for driving the pump 15 and a second motor drive 18 for driving the fluid-connection selector 9, these motor drives being controlled by a central monitoring and control unit 19 mounted on the frame 16, or, in a variant, mounted on the enclosure of the mixing apparatus 1.

More particularly, the first motor drive 17 of the pump 15 comprises a first motor 20 and a first transmission assembly 21 connected to the pump 15, which transmission assembly is, in this example, in the form of a first pair of gear wheels 22, 23 that mesh together, one of which (22) is connected to the pump 15, and the other which (23) is connected to the first motor 20, as can be seen more clearly in FIG. 2.

Similarly, the second motor drive 18 of the fluid-connection selector 9 comprises a second motor 24 and a second transmission assembly 25 connected to the fluid-connection selector 9, which assembly is, in this example, in the form of a second pair of gear wheels 26, 27 that mesh together, one of which (26) is connected to the moving portion 11 of the fluid-connection selector 9, and the other which (27) is connected to the second motor 24. Thus, when the motor drive 18 drives the gear wheel 27 in rotation, the gear wheel 26 is driven as indicated by the double-headed arrow F1 shown in FIG. 2 in order to put the various channels of the network of channels 12 into register with one another selectively, as described below.

The term "central monitoring and control unit" 19 is used to mean all of the components necessary for the mixing apparatus 1 to operate automatically, in particular one or more microcontrollers for the motors and the necessary internal interconnections. In addition, the mixing apparatus 1 includes, on the frame 16, and/or on the enclosure of the mixing apparatus 1, a user interface 19A with control buttons and/or a display, as well as a power supply 19B.

Advantageously, the mixing apparatus 1 may also include, on the frame 16 and/or on the enclosure of the device 1, one or more sensors 19D, e.g. a sensor for sensing presence of the first and second fluid reservoirs 3, 2, presence of fluid, presence of the patient, or presence of the needle 14, or else a detector for detecting structural integrity of the mixing apparatus 1, as well as an internal database 19C accessible to the central monitoring and control unit 19 and/or a radiofrequency transceiver 19E for data interchange with a remote computer (not shown).

It is also advantageously possible to provide the mixing apparatus 1 with locking apparatus (not shown) for locking the first and second reservoirs 3, 2 in place on the end-pieces provided with the first and second orifices 7, 6 in order to avoid any risk of the first and second reservoirs 3, 2 being exchanged or contaminated during or after use of the mixing apparatus 1.

Advantageously, the mixing apparatus 1 of the invention may be made up of two distinct assemblies 4, 5 fitting into each other, as appears clearly in FIG. 2. A disposable first assembly 4 comprising all of the portions of the mixing apparatus 1 that are in contact with the ingredients to be mixed is designed to be sterilized and to be a single-use assembly. A reusable second assembly 5 including the remainder of the mixing apparatus 1 is reusable. Thus, after the mixing apparatus 1 has been used, the disposable first assembly 4 is soiled and can be discarded, and the reusable second assembly 5 can be reused with a sterile other disposable first assembly 4 for preparing a new mixture.

Thus, the reusable second assembly 5 of the mixing apparatus 1 essentially comprises the frame 16 with the two motor drives 17, 18, and the central monitoring and control unit 19, while the disposable first assembly 4 comprises only the fluid-connection portions of the mixing apparatus 1, namely, in particular, the pump 15 and the fluid-connection selector 9 that are mounted on the stand 8.

It can be understood that the disposable first assembly 4 includes the gear wheel 22 connected to the pump 15 of the first motor drive 17 and the gear wheel 26 fastened to the moving portion 11 of the second motor drive 18, while the reusable second assembly 5 includes the gear wheel 23 connected to the motor drive 17 and the gear wheel 27 connected to the second motor drive 18.

By arranging the mixing apparatus 1 of the invention in the form of a disposable first assembly 4 and of a reusable second assembly 5 in this way, it is possible firstly to reduce the fluid-connection portion to be sterilized (disposable first assembly 4) and secondly to recycle the control and drive portion (reusable second assembly 5).

FIG. 3 shows the mixing apparatus 1 in section so as to show the moving elements of the mixing apparatus 1 more clearly. As can be seen, the pump 15 includes a piston 28 that, in this example, is equipped with a wormscrew co-operating with the gear wheel 22 of the pump 15. Thus, when the motor drive 17 drives the gear wheels 22, 23 of the first pair of gear wheels in rotation, the piston 28 moves longitudinally inside the pump 15 in one direction or the other, as indicated by the double-headed arrow F2 shown in FIG. 3 in order to cause the ingredients to flow through the apparatus 1.

Figure 4:
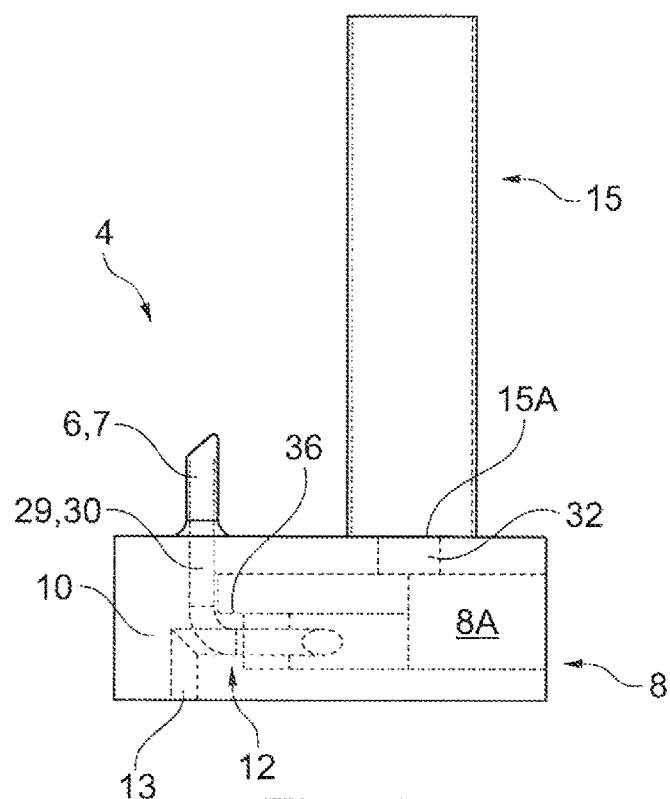
FIG. 4 shows a portion of the mixing apparatus of FIG. 1.
Figures 5, 6:
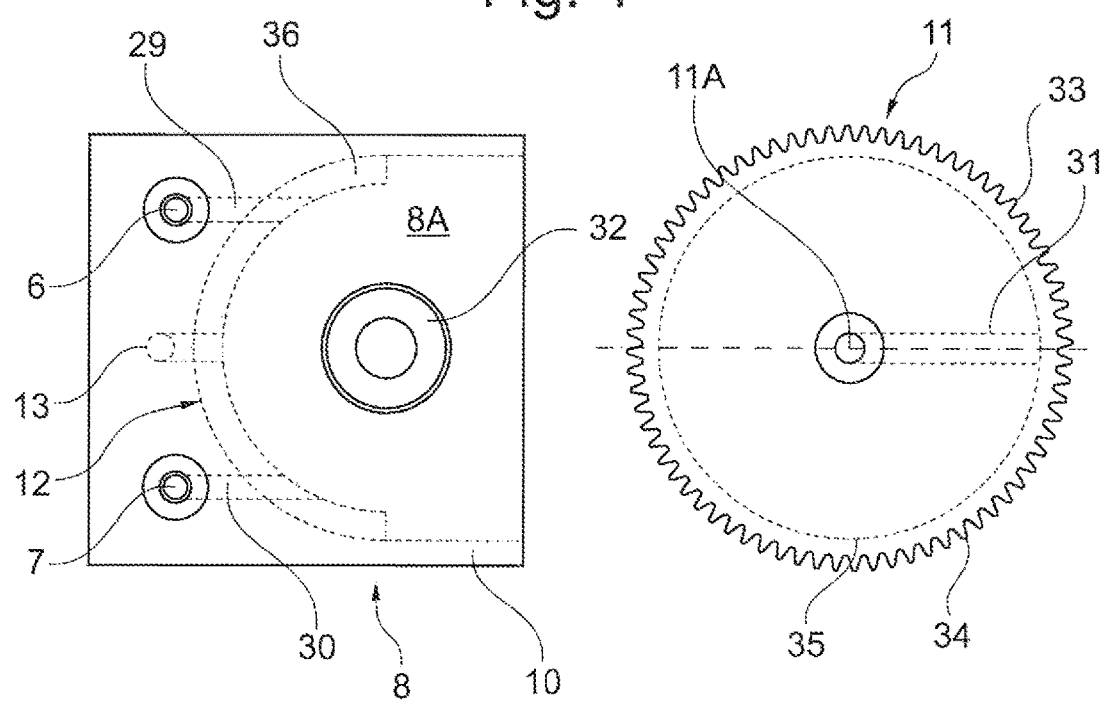
FIG. 5 shows another portion of the mixing apparatus of FIG. 1.
FIG. 6 shows yet another portion of the mixing apparatus of FIG. 1.

FIGS. 4 and 5 diagrammatically show the disposable first assembly 4 of the mixing apparatus 1, without the moving portion 11 of the fluid-connection selector 9, so as to show more clearly the network of channels 12 through which the ingredients can flow in the mixing apparatus 1. It can be seen that the stand 8 is provided with two first channels 29, 30 connected directly to respective ones of the end-pieces provided with the first and second orifices 7, 6, and opening out in the recess 8A of the stand 9, which recess is connected to the outlet channel 13. In addition, the stand 8 is provided with a third channel 32 opening out, at one end, into the port 15A of the pump 15, and, at the other end, into the recess 8A.

In addition, the moving portion 11 of the fluid-connection selector 9, which moving portion is circular in this example, is edged over its entire periphery with teeth 33 forming the gear wheel 26 of the second pair of gear wheels over a length segment 34 of the moving portion 11, as can be seen in FIG. 6. Over another length segment 35, the moving portion 11 is smooth, and set back slightly relative to the teeth 33, thereby giving the moving portion 11 a T-shaped profile as seen in axial section through the moving portion 11 in FIG. 3. The recess 8A in the stand 8 is of shape complementary to the shape of the moving portion 11, with a semicircular sill 36 that can be seen more clearly in FIG. 5, and on which the toothed length segment 34 of the moving portion 11 rests. In a variant, the teeth 33 of the gear wheel 26 extend over only a fraction of the periphery of the moving portion 11 so as to form an abutment and so as to limit the extent to which the moving portion 11 can move in rotation in the stationary portion 10.

As can be seen more clearly in FIGS. 3 and 6, the moving portion 11 is provided with an L-shaped channel 31 that passes through the center 11A of the moving portion 11 and that opens out laterally at the smooth length segment 35 of the moving portion 11.

Thus, when the moving portion 11 is in position in the recess 8A of the stand 8, the channel 31 opens out at the center into the third channel 32 leading to the pump 15. The moving portion 11 can then occupy three different angular positions for connecting the pump 15 selectively and in sealed manner to the outlet channel 13 or to each of the end-pieces provided with the first and second orifices 7, 6, the channel 31 opening out laterally into the outlet channel 13 or into one or the other of the first channels 29, 30 leading to the end-pieces provided with the first and second orifices 7, 6. This circular arrangement of the fluid-connection selector 9 makes it possible to distribute the fluid pressure properly in the network of channels 12, and to obtain good sealing for the fluid-connection selector 9, while also reducing the number of component parts of said fluid-connection selector.

Figure 7:
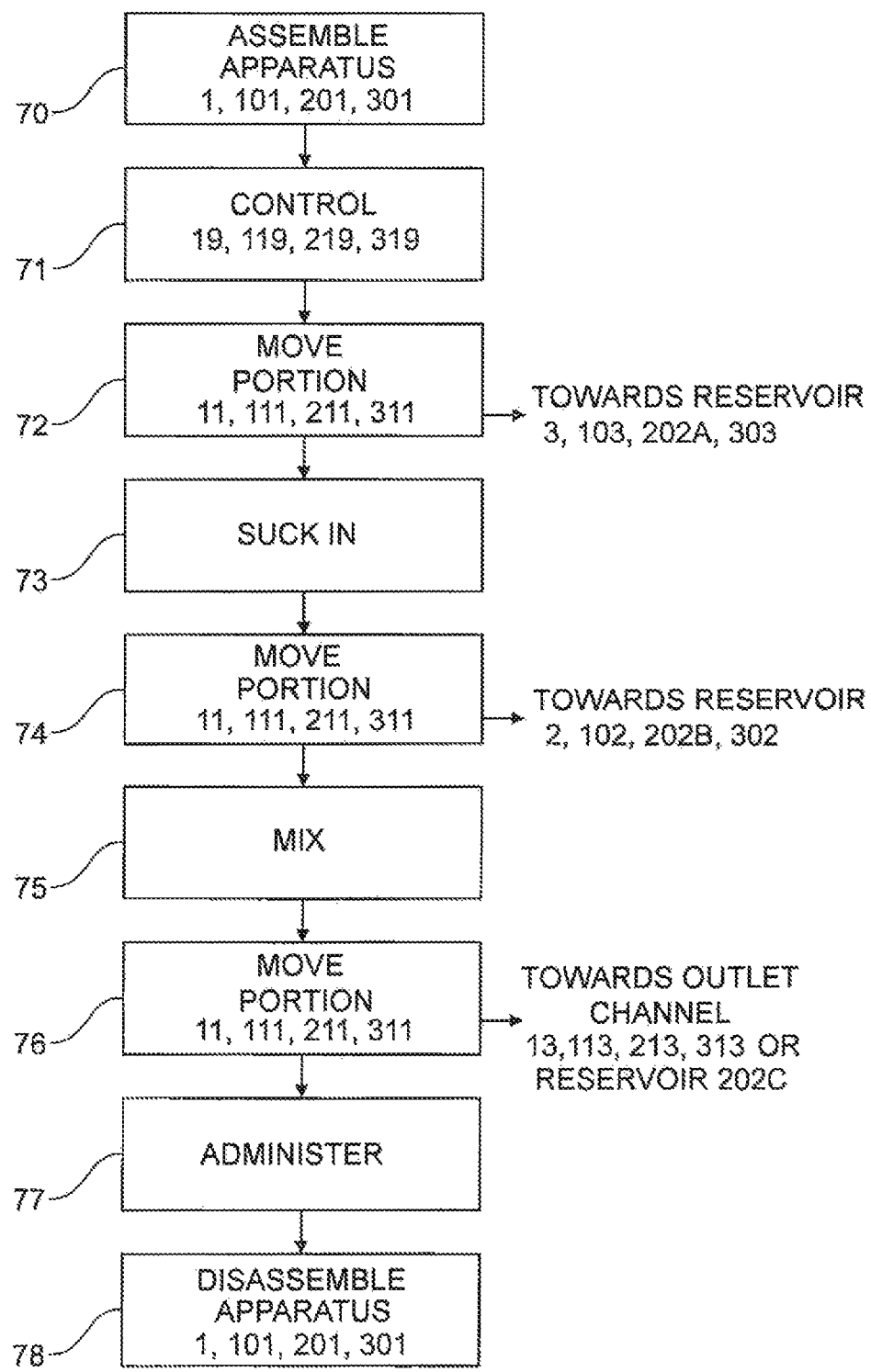
FIG. 7 is a flow chart representing the steps for using the mixing apparatus of the invention.

In order to use the mixing apparatus 1 of the invention and in order to mix and blend the two ingredients contained in the first and second reservoirs 2, 3, the user starts, in step 70 of FIG. 7 by fitting the first and second reservoirs 3, 2 over respective end-pieces provided with respective ones of first and second orifices 7, 6, with, for example, a solid powder or a "lyophilized" substance in the second reservoir 2 and a solvent in the first reservoir 3, and by assembling the mixing apparatus 1 by fitting the disposable first assembly 4 and the reusable second assembly 5 into each other.

Then, in step 71, the user actuates the central unit 19 for triggering the mixing steps 72 to 76 of that are advantageously pre-programmed in the central monitoring and control unit 19. Advantageously, in said step 72, the central monitoring and control unit 19 accesses the internal database 19C or an external database via the transceiver 19E so as to act on the basis of information given by the user via the user interface 19A or supplied by the sensors 19D to determine the protocol of the mixing, e.g. the metered quantity of solvent to be used, and optionally the injection protocol, e.g. the depth of penetration of the needle 14 into the skin, the speed of injection, etc.

In step 72, the central monitoring and control unit 19 causes the moving portion 11 of the fluid-connection selector 9 to move in rotation so as to put the channel 31 of the moving portion 11 into register with the channel 30 leading to the end-piece provided with the first orifice 7 of the solvent first reservoir 3.

In the suction step 73, the central monitoring and control unit 19 then actuates the drive 17 of the pump 15, thereby driving the piston 28, so as to suck the desired metered quantity of solvent into the pump 15.

Then, once the necessary quantity of solvent has been sucked in, in step 74, the central monitoring and control unit 19 causes the moving portion 11 of the fluid-connection selector 9 to move in rotation once again so as to put the channel 31 of the moving portion 11 into register this time with the channel 29 leading to the end-piece provided with the second orifice 6 of the second reservoir 2 containing solid powder, or a lyophilized substance.

In the blending step 75, the central monitoring and control unit 19 actuates the drive 17 of the pump 15 so as to inject the solvent, contained in the pump 15, into the second reservoir 2. Depending on the ingredients present, the mixing protocol can require blending of the mixture in order to a obtain a homogeneous mixture. In such a situation, the piston 28 of the pump 15 can be actuated in both directions of the arrow F2 shown in FIG. 3 in order to suck in and to deliver the mixture a plurality of times from/towards the second reservoir 2. This blending also makes it possible to ensure that only the homogeneous mixture is present in the mixing apparatus 1, and in particular that there does not remain any trace of pure solvent that might be injected as it is. The accuracy of the metering of active ingredient of the mixture is thus improved. Once the mixture is homogeneous in compliance with the protocol, the mixture is sucked into the pump 15. Whereupon, with a view to administering the mixture to a patient, the mixture can either be stored in one of the first and second reservoirs 3, 2, or in the pump 15 which then constitutes a pump reservoir, or else be discharged via the outlet channel 13 of the mixing apparatus 1 as described below.

In a first operating mode, the mixture is designed to be stored in one of the first and second reservoirs 3, 2, in order to be used subsequently. In this mode, after the step 75, step 78 is performed, during which the disposable first assembly 4 is disunited from the reusable second assembly 5, and the first and/or second reservoirs 3, 2 are removed from the end-pieces provided with respective ones of the first and second orifices 6, 7 so that the second container 2 containing the mixture can be kept. The first and second reservoirs 3, 2 can also be taken without disuniting the disposable first assembly 4 from the reusable second assembly 5.

In a second operating mode, in order to discharge the mixture, in step 76, the central monitoring and control unit 19 causes the moving portion 11 of the fluid-connection selector 9 to move in rotation so as to put the channel 31 of the moving portion 11 into register with the outlet channel 13. The mixture can then be discharged from the mixing apparatus 1, and administered to the patient in compliance with the protocol. The mixture can also be transferred to any container suitable for subsequently administering the mixture and/or for storing it.

When the mixture is to be injected to a patient, directly using the mixing apparatus 1, said mixing apparatus 1 is placed, in step 77, by the user, e.g. by the patient, at the location on the patient where the mixture is to be injected. In compliance with the information received by the sensors 19D and from the internal database 19C or external database, the central monitoring and control unit 19 causes the needle 14 to be moved in the axial direction A in order to pierce the skin of the patient to the desired depth. The pump 15 is then actuated by the central monitoring and control unit 19 and the mixture is injected. At the end of the injection, and also in compliance with the information from the sensors 19D and from the databases, the monitoring and control unit 19 stops the pump 15 and causes the needle 14 to be withdrawn.

Since the mixing and the injection are finished, the user can, in step 78, disunite the disposable and reusable first and second assemblies 4 and 5, the disposable first assembly 4 then being treated as medical waste, and the second assembly 5 being ready to perform another ingredient-mixing operation.

Thus, with the mixing apparatus 1 of the invention, the user can easily mix two ingredients and blend the resulting mixture to obtain a homogeneous solution without using parts other than the mixing apparatus 1 itself. Handling the mixing apparatus 1 of the invention is reduced to three main steps that consist, for the user: firstly in mounting the disposable portions (disposable first assembly 4 and first and second reservoirs 3, 2) on the reusable portion (reusable second assembly 5); secondly in actuating the central monitoring and control unit 19 so as to trigger the fully automated mixing/blending; and thirdly in administering the mixture or in transferring it or storing it. This considerably limits the time spent and the risks of error, and also the risk of injury, or of contamination in the event that the active substance is dangerous for the operator, such as, for example, with cytotoxic substances. In addition, by means of the central monitoring and control unit 19 that manages actuation of the pump 15, the metering of the ingredients is very accurate and good blending of the mixture is achieved.

Figure 9:
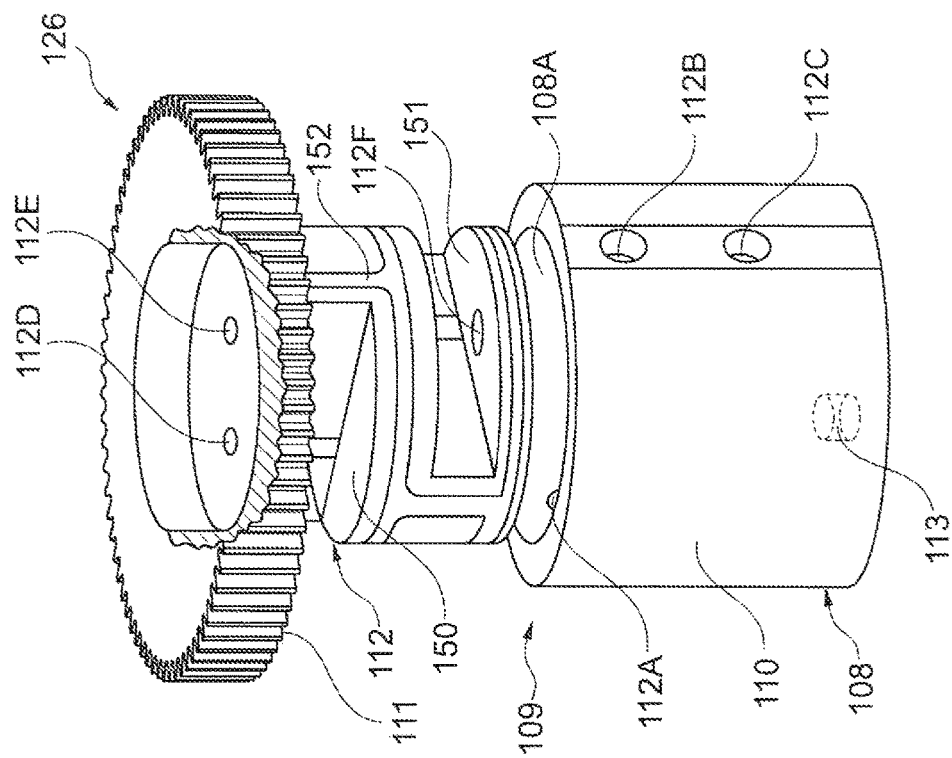
FIG. 9 is an enlarged view of a portion of the mixing apparatus of FIG. 8.
Figure 8:
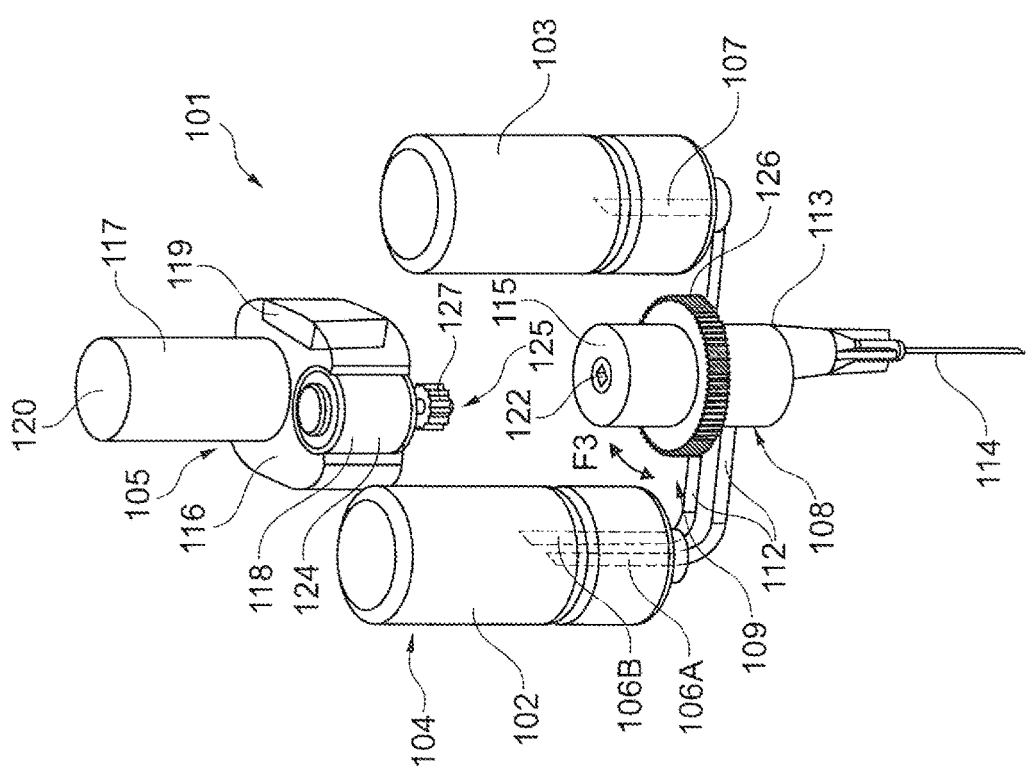
FIG. 8 is an exploded perspective view of a second embodiment of the mixing apparatus of the invention.

With reference to FIGS. 8 and 9, a second embodiment of the mixing apparatus of the invention is described below. Thus, FIG. 8 shows mixing apparatus 101 of the invention, and the elements that are common to the mixing apparatus 1 and to the mixing apparatus 101 and that perform the same functions are assigned the same reference numerals plus 100. For reasons of clarity and concision, the following description essentially describes the elements of the mixing apparatus 101 that differ from the above-described mixing apparatus 1.

As shown in FIG. 8, the mixing apparatus 101 includes a stand 108 on which the following are mounted: a second reservoir 102 connected to a pair of end-pieces provided with second orifices 106A, 106B in sealed manner; a first reservoir 103 connected to another end-piece provided with a first orifice 107 in sealed manner, and an outlet channel 113 for discharging the mixture, e.g. via an injection needle 114. The stand 108 also receives a rotary fluid-connection selector 109 that is described below with reference to FIG. 9.

As can also be seen in FIG. 8, the mixing apparatus 101 also includes a motor-driven pump 115 mounted on the stand 108, which pump is, in this example, of the one-directional type having two ports (not shown), and is adapted to cause the ingredients to flow through the fluid-connection selector 109 between the first and second reservoirs 103, 102 and the outlet channel 113.

In addition, the mixing apparatus 101 further includes, on a frame 116, a first motor drive 117 for driving the pump 115 and a second motor drive 118 for driving the fluid-connection selector 109, these motor drives being controlled by a central monitoring and control unit 119 mounted on the frame 116.

In the mixing apparatus 101, the first motor drive 117 of the pump 115 comprises a first motor 120 and a first transmission assembly 121 connected to the pump 115, which transmission assembly is, in this example, in the form of a square inter-fitting coupling 122. The first transmission assembly 121 could also be in some other form of the latch type making it possible to drive the pump 115. In this example, the second motor drive 118 of the fluid-connection selector 109 comprises a second motor 124 and a second transmission assembly 125 comprising a pair of gear wheels 126, 127 that mesh together, one of which (126) is fastened to the moving portion 111, the gear wheel 127 being connected to the second motor drive 118. Thus, when the gear wheel 127 is driven in rotation by the second motor drive 118, said gear wheel drives the gear wheel 126 in rotation as indicated by the double-headed arrow F3 shown in FIG. 8, so as to put the channels of the network of channels 112 of the fluid-connection selector 109 into register with one another, as described below.

As can be seen more clearly in FIG. 9, the stand 108 constitutes a stationary portion 110 of the fluid-connection selector 109 that is significantly different from the fluid-connection selector 9 of the above-described mixing apparatus 1. In this example, the stand 108, which is substantially cylindrical, is provided with a recess 108A that is also substantially cylindrical, that is connected to the outlet channel 113, and that is suitable for receiving a moving portion 111 of the fluid-connection selector 109, which is also substantially cylindrical, and the stand 108 is also provided with a network of channels 112 that can be put into register with one another so as to connect the end-pieces provided with second orifices 106A, 106B, 107 selectively to the outlet channel 113.

More precisely, three channels 112A, 112B, 112C are formed in the periphery of the stationary portion 110 of the fluid-connection selector 109, these channels 112A, 112B, 112C being connected at one end respectively to the end-piece provided with the first orifice 106 and to the end-pieces provided with the second orifices 106A, 106B, and opening out at the other end into the recess 108A. In addition, two semi-cylindrical recesses 150, 151 that are perpendicular to each other are formed laterally in the moving portion 111 of the fluid-connection selector 109, each recess 150, 151 being extended by a respective channel 112D, 112E connected to a port of the pump 115. A set of gaskets 152 are disposed around the recesses 150, 151 for fully sealing the fluid-connection selector 109.

In addition, the moving portion 111 has a head forming the gear wheel 126 that is of larger diameter than the stand 108 that it can be driven by the gear wheel 127.

While the fluid-connection selector 109 is operating, the moving portion 111 is inserted into the stationary portion 110 and can take up three angular positions for selectively connecting the outlet channel 113 or the second and first orifices 106A, 106B, 107 to the pump 115 or together.

When the moving portion 111 is in a first angular position in the stationary portion 110, the channel 112A leading to the end-piece provided with the first orifice 107 of the first reservoir 103 coincides with the recess 150 and with the channel 112D leading to the pump 115, and the channel 112C leading to the end-piece provided with the second orifice 106A of the second reservoir 102 coincides with the recess 151 and with the channel 112E leading to the pump 115, so as to put the first and second reservoirs 103, 102 into fluid connection with each other, and so as to transfer an ingredient from the first reservoir 103 to the second reservoir 102 or from the second reservoir 102 to the first reservoir 103. The other two channels 112B and 113 are closed off in this first position.

When the moving portion 111 is in a second angular position, the two channels 112B, 112C leading to the end-pieces provided with the second orifices 106A, 106B of the second reservoir 102 coincide respectively with the recesses 150 and 151, so as to put these two end-pieces provided with the second orifices 106A, 106B into fluid connection with each other, via the channels 112D, 112E and via the pump 115, so as to blend the mixture in the second reservoir 102, for example. The channels 112A and 113 are closed off in this second position. In order to facilitate the fluid flow, the end-pieces carrying the second orifices 106A, 106B have different lengths and/or have end sections of different inside dimensions. To this end, and by way of example, when a liquid of viscosity of about 1 centipoise (cP) is used, the second orifice used for suction preferably presents an end section with a diameter of about 0.39 millimeters (mm), and the second orifice used for delivery presents a terminal section of diameter of about 0.24 mm, for a flow-rate of 0.26 milliliters per second (mL/s) in a reservoir of 5 mL disposed no more than 8 mm under the surface of the liquid present, e.g. 2.5 mL. On being put back into the second reservoir 102, the liquid is thus thrust with force to the extent it reaches the wall of the second reservoir 102, thereby facilitating washing out of the second reservoir 102 as well as facilitating blending.

Finally, when the moving portion 111 is in a third angular position, the channel 112B leading to the end-piece provided with the second orifice 106B of the second reservoir 102 coincides with the recess 150 and with the channel 112D leading to the pump 115, and the channel 112E from the pump 115 coincides with the outlet channel 113, so as to put the second reservoir 102 into fluid connection with the outlet and thus so as to discharge the mixture. The other two channels 112A and 112C are closed off in this third position.

The mixing apparatus 101 of the invention is preferably made up of two assemblies 104, 105 that fit into each other, the disposable first assembly 104 being designed to be sterilized and to be a single-use assembly, and the reusable second assembly 105 being suitable for being reused. Thus, the disposable first assembly 104 includes the fluid-connection portions of the mixing apparatus 101 such as in particular the pump 115, the fluid-connection selector 109, and the stand 108, and the reusable second assembly 105 includes the frame 116 with the motor drives 117, 118 and the central monitoring and control unit 119.

With reference to FIG. 7, use of the mixing apparatus 101 of the invention is described below for mixing an ingredient in solid powder form or in lyophilized form contained in the second reservoir 102 with a solvent contained in the first reservoir 103, it being understood that only the variations relative to the mixing apparatus 1 are described in detail.

After fitting the first and second reservoirs 3, 2 over the end-pieces provided with second and first orifices 106A, 106B, 107 (step 70), in step 71 the user actuates the central monitoring and control unit 119 to trigger the mixing and blending steps 72 to 76.

In step 72, the central unit causes the moving portion 111 of the fluid-connection selector 109 to move in rotation into the above-described first angular position. When, in the suction step 73, the central monitoring and control unit 119 actuates the drive 117 of the pump 115, the solvent contained in the first reservoir 103 is sucked in by the pump 115 and directed into the second reservoir 102.

Then, in step 74, the central monitoring and control unit 119 causes the moving portion 111 of the fluid-connection selector 109 to move in rotation again, into the above-described second angular position. Thus, in the blending step 75, the pump 115 causes the mixture of solid powder in suspension or of the lyophilized ingredient as rehydrated with the solvent to flow between the end-pieces provided with the second orifices 106A, 106B of the second reservoir 102 in order to blend the mixture.

Finally, in a first operating mode, once the mixture is homogeneous, in compliance with the protocol, the central monitoring and control unit 119 can, in step 76, cause the moving portion 111 of the fluid-connection selector 109 to move in rotation, so that it takes up its above-described third angular position, with a view to discharging the mixture.

In a second operating mode, it is also possible to store the resulting mixture in the second reservoir 102.

With reference to FIGS. 10 to 13, a third embodiment of the mixing apparatus of the invention is described below. Thus, FIG. 10 shows mixing apparatus 201 of the invention, and the elements that are common to the mixing apparatus 1 and to the mixing apparatus 201 and that perform the same functions are assigned the same reference numerals plus 200. Thus, as above, the following description mainly describes the elements of the mixing apparatus 201 that differ from the above-described mixing apparatus 1.

The mixing apparatus 201 is designed to mix and to blend the ingredients in first, second, and third standard medical reservoirs 202A, 202B, 202C, there thus being three such reservoirs in this example.

As can be seen in FIG. 10, the mixing apparatus 201 includes a stand 208 carrying a moving slide 211 mounted to slide in a direction F4 indicated in FIG. 10 in a stationary slideway 210 that is formed by a linear fluid-connection selector 209 and by a network of channels 212.

More precisely, the slide 211 has an upside down channel-section profile that slides in two grooves 210A, 210B of the slideway 210, which is in the shape of an E lying on its side. In this example, the web of the channel section of the slide 211 is provided with four through orifices 229A, 229B, 229C, 229D that are disposed in a row in the direction F4, that can be seen more clearly in FIG. 12, and that are extended by respective ones of four end-pieces, provided with first, second, and third orifices 206A, 206B, 206C, 206D, and suitable for receiving the first, second, and third reservoirs 202A, 202B, 202C in sealed manner as described below. As shown in FIG. 11, the end-pieces provided with the second orifices 206B, 206C for the second reservoir 202B advantageously have differences in length and/or in inside end section dimensions (e.g. in inside diameters) in order to improve the fluid flow through the second reservoir 202B.

The slideway 210 is provided with an outlet channel 213 for discharging the mixture, in this example via an injection needle 214 that is mounted to move relative to the stand 208. As explained below, more particularly with reference to FIG. 11, the end-pieces provided with the first, second, and third orifices 206A, 206B, 206C, 206D and the outlet channel 213 can be interconnected selectively via the network of channels 212 of the fluid-connection selector 209.

In a manner similar to the above-described mixing apparatus 1 and mixing apparatus 101, the mixing apparatus 201 includes, mounted on the stand 208, a motor-driven pump 215, of the two-directional type having two ports (not shown), adapted to cause the ingredients to flow through the network of channels 212, between the end-pieces provided with the first, second, and third orifices 206A, 206B, 206C, 206D and the outlet channel 213.

As can also be seen in FIG. 10, the mixing apparatus 201 further includes, on a frame 216, a first motor drive 217 for driving the pump 215 and a second motor drive 218 for driving the fluid-connection selector 209, these motor drives being controlled by a central monitoring and control unit 219 mounted on the frame 216.

More particularly, the first motor drive 217 of the pump 215 comprises a first motor 220 and a first transmission assembly 221 connected to the pump 215, which transmission assembly is, in this example, in the form of a square inter-fitting coupling. The second motor drive 218 of the fluid-connection selector 209 comprises a second motor 224 and a second transmission assembly 225 connected to the fluid selector 209, which assembly is, in this example, in the form of a gear wheel 227 that is connected to the motor 224 and that co-operates with a rack 226 (shown in FIG. 13) formed on the slide 211 of the fluid-connection selector 209. Thus, when the motor drive 218 drives the gear wheel 227 in rotation, the slide 211 slides as indicated by the double-headed arrow F4 in order to put the various channels of the network of channels 212 into register with one another selectively, as described below.

It can be understood that the apparatus 201 of the invention is made up of two distinct assemblies that fit into each other and that are detachable, a disposable first assembly 204 including the portions of the mixing apparatus 201 that are in contact with the ingredients to be mixed, namely, in particular, the stand 208, the fluid-connection selector 209, and the pump 215, and a reusable second assembly 205 including, in particular, the respective motor drives 217, 218 of the pump 215 and of the fluid connection selector 209.

In FIG. 11, the mixing apparatus 201 is shown in section so as to show the network of channels 212 of the mixing apparatus 201 more clearly. In particular, a U-shaped channel 232 connected to the pump 215 is formed in the slideway 210, this channel 232 opening out into two orifices 232A, 232B facing the slide 211.

Figure 12:
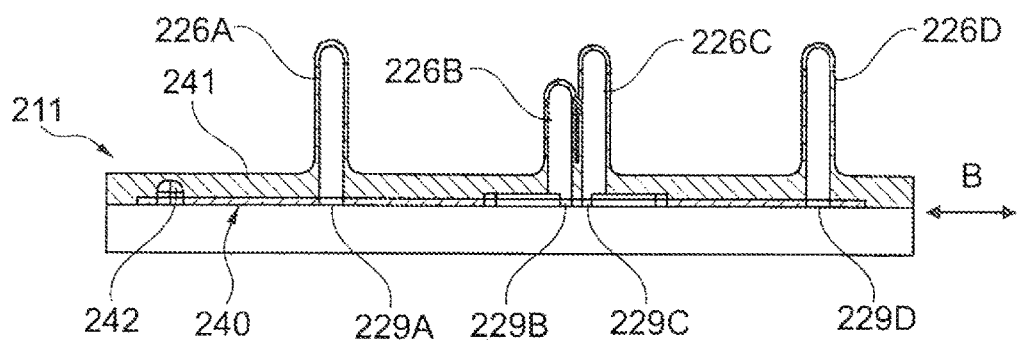
FIG. 12 is an enlarged view on a vertical plane containing the axis XI-XI of FIG. 10, showing a portion of the mixing apparatus of FIG. 10.

FIG. 12 shows the slide 211 in section, provided with a central recess 240 that extends over a portion of the length of the slide 211 and that surrounds the orifices 229A to 229D and a blind, oblong fifth orifice 242 in alignment with the row of orifices 229A to 229 in the direction F4 (shown in FIG. 11). In the recess 240, an intermediate part 241 is shown that is of shape complementary to the shape of the recess 240, that is designed to be interposed between the slide 211 and the slideway 210 when the slide 211 is mounted in the slideway 210, and that serves as a fluid-connection guide and as a gasket.

Figure 13:
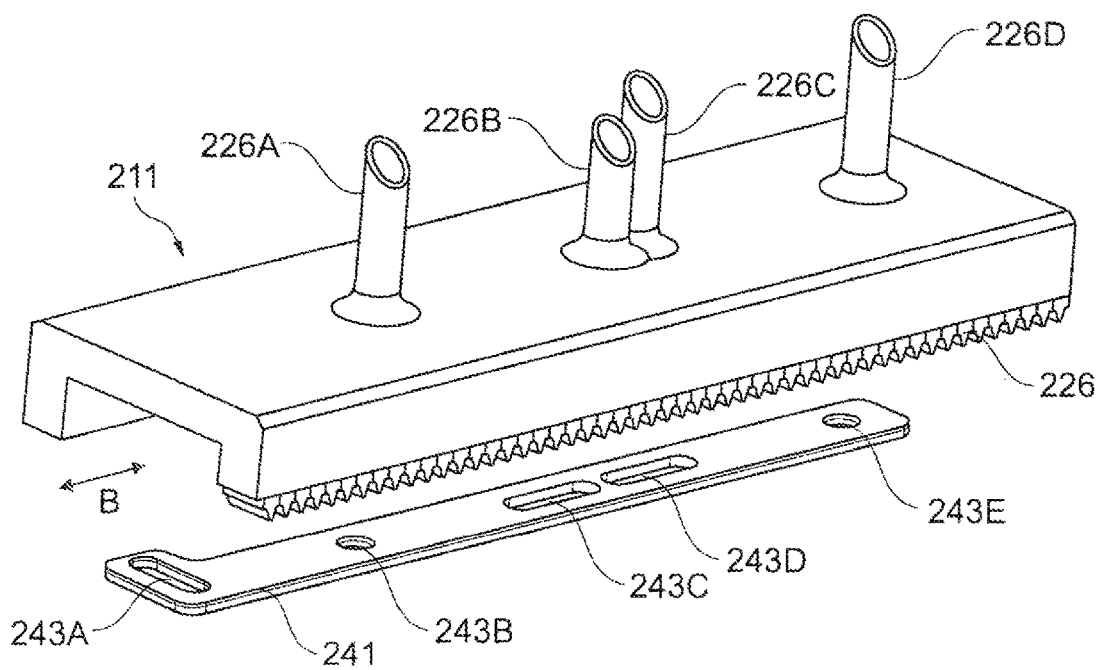
FIG. 13 is an enlarged perspective view of the FIG. 12 portion of the mixing apparatus.

FIG. 13 shows the intermediate part 241 more clearly, which part is provided with five orifices 243A, 243B, 243C, 243D, and 243E that are disposed in a row and that coincide respectively with the blind hole 242, and with the orifices 229A to 229D when the intermediate part 241 is inserted into the recess 240, three orifices 243A, 243C, 243D being oblong and two orifices 243A, 243D being substantially circular. It can also be seen that the intermediate part 240 forms an extension in a direction substantially perpendicular to the direction F4, in which extension the oblong orifice 243A extends (the blind orifice 242 also extending in the same perpendicular direction), the other two oblong orifices 243C, 243D extending in the direction F4.

It can be understood that the mixing apparatus 201 is equipped at the various channels of the network of channels 212 with appropriate sealing elements (not shown).

Thus, when the slide 211 with the intermediate part 241 is in position in the slideway 210, the orifices 232A, 232B of the channel 232 coming from the pump 215 can be put into communication with two adjacent orifices 242, 229A to 229D of the slide 211 so as to connect the pump 215 selectively to one or two of the first, second, and third reservoirs 202A, 202B, 202C and/or to the outlet channel 213. In particular, it is possible, in this example, to define four different lateral positions for the slide 211 in the slideway 210.

When the slide 211 is in an initial lateral position in the slideway 210 that is shown in FIG. 11, the channel 232 puts the end-piece provided with the first orifice 206A of the first reservoir 202A into communication with the blind orifice 242 of the slide 211, which blind orifice is connected to the outlet channel 213, so as to put the first reservoir 202A into fluid connection with the outlet, and thus so as to discharge the contents of said first reservoir. The other end-pieces provided with the second and third orifices 206B, 206C, 206D of the other two, second and third, reservoirs 202B, 202C are closed off in this first position.

When the slide 211 is in a first lateral position, the channel 232 puts the end-piece provided with the first orifice 206A of the first reservoir 202A into communication with the end-piece provided with the second orifice 206B of the second reservoir 202B, so as to interconnect these two first and second reservoirs 202A, 202B so as to transfer an ingredient from the first reservoir 202A to the second reservoir 202B, or vice versa. The outlet channel 213 and the end-pieces provided with the second and third orifices 206C, 206D are closed off in this second position.

When the slide 211 is in a second lateral position, the channel 232 puts the two end-pieces provided with the second orifices 206B, 206C of the second reservoir 202B into communication, so as to blend the mixture in the second reservoir 202B. The outlet channel 213 and the end-pieces provided with the second orifices 206A, 206D are closed off in this third position.

Finally, when the slide 211 is in a third lateral position, the channel 232 puts the end-piece 206C of the second reservoir 202B into communication with the end-piece provided with the third orifice 206D of the third reservoir 202C, so as to put these second and third reservoirs 202B, 202C into fluid connection with each other so as to transfer an ingredient or the mixture from the second reservoir 202B to the third reservoir 202C, or vice versa. The outlet channel 213 and the end-pieces provided with the first and second orifices 206A, 206B are closed off in this fourth position.

Use of the mixing apparatus 201 of the invention is described below with reference to FIG. 7, only the variations relative to the mixing apparatus 1 being described, the main steps being same as those described above for the mixing apparatus 1. The mixing apparatus 201 may be used to mix and to blend an ingredient in solid powder form or in lyophilized form contained in the second reservoir 202B with a solvent contained in the first reservoir 202A, and then to discharge the mixture either into a third reservoir 202C, or towards the outlet channel 213 and the needle 214.

After fitting the first, second, and third reservoirs 202A, 202B, 202C over the end-pieces provided with the first, second and third orifices 206A, 206B, 206C, 206D (step 70), in step 71 the user actuates the central monitoring and control unit 219 to trigger the mixing steps 72 to 76.

In step 72, the central monitoring and control unit 219 causes the slide 211 of the fluid-connection selector 209 to move in rotation into the above-described second lateral position. When, in the suction step 73, the central monitoring and control unit 219 actuates the drive 217 of the pump 215, the solvent contained in the first reservoir 202A is sucked in by the pump 215 and directed into the second reservoir 202B.

Then, in step 74, the central monitoring and control unit 219 causes the slide 211 to move laterally again, into the above-described third lateral position. Thus, in the blending step 75, the pump 215 causes the mixture to flow between the two end-pieces provided with the second orifices 206B, 206C of the second reservoir 202B in order to blend the mixture in said second reservoir 202B.

Once the mixture is homogeneous, in step 76 the central monitoring and control unit 219 causes the slide 211 to move laterally into the above-described third lateral position, with a view to administering the mixture either directly via the outlet channel 213, or indirectly via the third reservoir 202C.

A fourth embodiment of the mixing apparatus of the invention is described below with reference to FIGS. 14 to 16. FIG. 14 shows mixing apparatus 301 of the invention, and the elements that are common to the mixing apparatus 1 and to the mixing apparatus 301 and that perform the same functions are assigned the same reference numerals plus 300. Thus, as above, the following description mainly describes the elements of the mixing apparatus 301 that differ from the above-described mixing apparatus 1.

FIG. 14 shows mixing apparatus 301 including a stand 308 on which first and second reservoirs 303, 302 are mounted that are connected in sealed manner to respective end-pieces provided with respective ones of first and second orifices 307, 306 (shown in FIG. 16), and which is provided with an outlet channel 313 for discharging the mixture via an injection needle 314. The stand 108 also comprises a linear fluid-connection selector 309 including a network of channels 312 that can be put into register so as to connect the first and second reservoirs 303, 302 to the outlet channel 313 selectively, as described below with reference to FIGS. 15 and 16.

The mixing apparatus 301 also includes a motor-driven pump 315 mounted on the stand 308. In this example, this pump is of the two-directional pump type having a piston 328 and a single port 315A visible in FIG. 16, and is adapted to cause the ingredients to flow through the fluid-connection selector 309, between the end-pieces provided with first and second orifices 306, 307 and the outlet channel 313.

As can also be seen in FIG. 14, the mixing apparatus 301 further includes a frame 316 on which a first motor drive 317 for driving the pump 315 and a second motor drive 318 for driving the fluid selector 309 are mounted, these motor drives being controlled by a central monitoring and control unit 319 also mounted on the frame 316.

More particularly, the first motor drive 317 of the pump 315 comprises a first motor 320 and a first transmission assembly 321 connected to the pump 315, which transmission assembly is, in this example, in the form of a first pair of gear wheels 322, 323 that mesh together, one of which (322) is connected to the pump 315, and the other which (323) is connected to the first motor drive 317.

Similarly, the second motor drive 318 of the fluid-connection selector 309 comprises a second motor 324 and a second transmission assembly 325 connected to the fluid-connection selector 309, which assembly is, in this example, in the form of a gear wheel 327 that is connected to the motor 324 and that co-operates with a rack 326 (shown in FIG. 13) formed on the fluid-connection selector 309.

Thus, when the motor drive 317 drives the gear wheels 322, 323 in rotation, the piston 328 moves longitudinally inside the pump 315 in one direction or the other as indicated by the double-headed arrow F5 shown in FIG. 14 in order to cause the ingredients to flow through the mixing apparatus 301.

As can be seen in FIG. 15, the stand 308 forms a stationary portion 310 of a linear fluid-connection selector 309 and is provided with a substantially cylindrical recess 308A so as to receive a substantially cylindrical moving portion 311 of the fluid-connection selector 309. Thus, when the motor drive 318 drives the gear wheel 327 in rotation, the rack 326 formed on the moving portion 311 is driven as indicated by the double-headed arrow F6 shown in FIG. 16 in order to put the various channels of the network of channels 312 of the fluid-connection selector 309 into register with one another, as described below.

Advantageously, the mixing apparatus 301 may also be made up of two distinct assemblies 304, 305 that fit into each other, as appears clearly in FIG. 14, the disposable first assembly 304 including all of the portions of the mixing apparatus 301 that are in contact with the ingredients to be mixed (in particular the pump 315, the fluid-connection selector 309, and the stand 308), and the reusable second assembly 305 including the remainder of the mixing apparatus 301 (in particular the frame 316, and the motor drives 317, 318).

Figure 16:
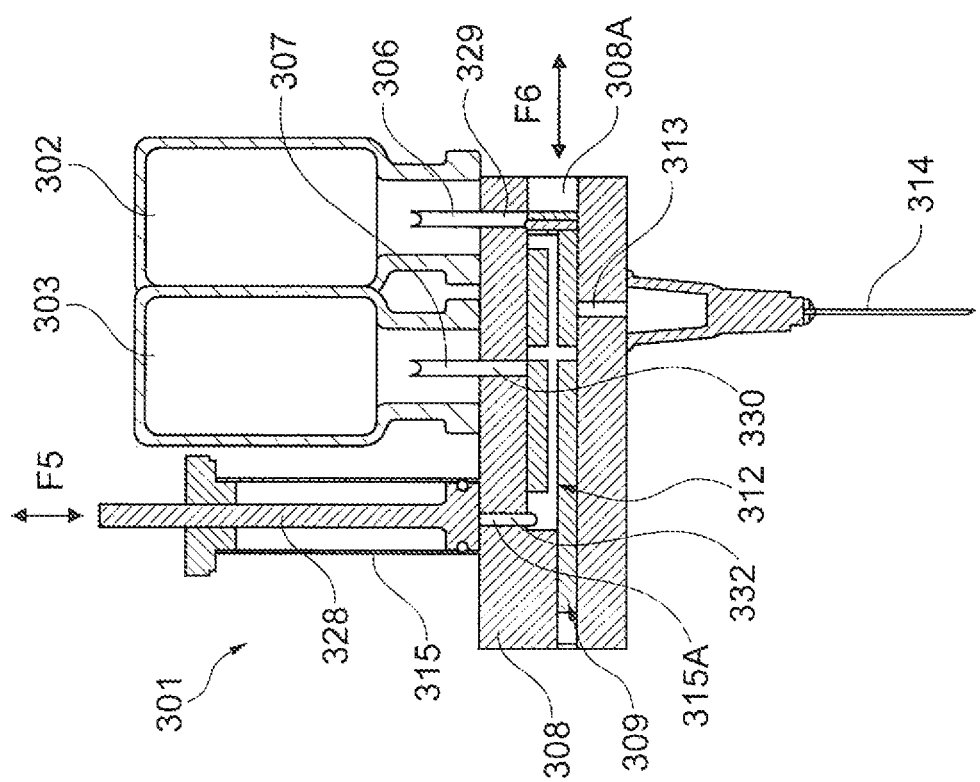
FIG. 16 is a section view on a vertical plane containing the axis XVI-XVI of FIG. 14, showing the mixing apparatus of FIG. 14.

As can be seen in FIG. 16, the stand 308 is provided with two first channels 329, 330 connected directly to respective ones of the end-pieces provided with the second and first orifices 306, 307 and opening out in the recess 308A of the stand 308. In addition, the stand 308 is provided with a third channel 332 putting the port 315A of the pump 315 and the recess 308A into communication with each other.

Figure 17:
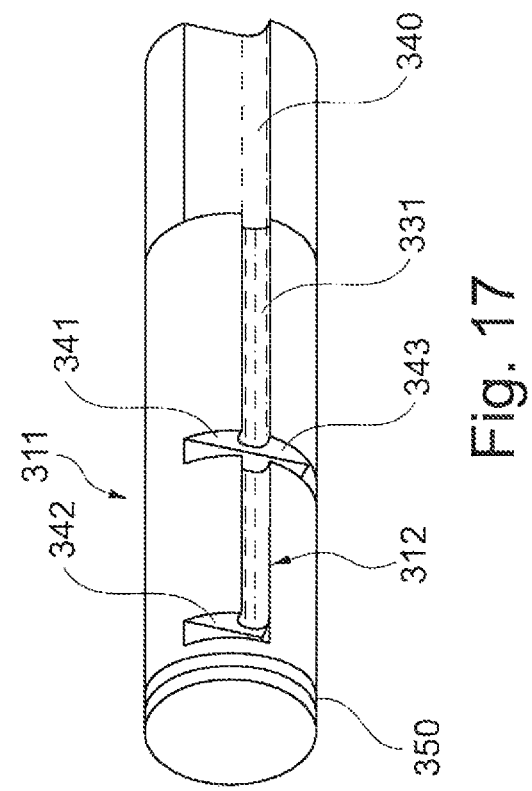
FIG. 17 is an enlarged perspective view of a portion of the mixing apparatus of FIG. 14.

FIG. 17 shows the moving portion 311 that is provided longitudinally over its periphery with a channel 331 that opens out laterally into four channel portions 340, 341, 342, 343 that are substantially perpendicular to the channel 331, a very wide first channel portion 340 being designed to communicate with the pump 315, and each of the other channel portions 341, 342, 323 being designed to connect a respective one of the channels 329, 330 leading to the second or third reservoirs 302, 303, or to connect the outlet channel 313.

In addition, the moving portion 311 is equipped at one end with a gasket 350 for closing the recess 308A of the fluid-connection selector 309 in sealed manner. It can be understood that the mixing apparatus 301 is equipped at the various channels of the network of channels 312 with appropriate sealing elements (not shown).

When the moving portion 311 is in position in the recess 308A as shown in FIG. 16, it can take up three different lateral positions depending on the direction indicated by the arrow F6 in FIG. 16. In all three of these lateral positions, the channel portion 340 remains in communication with the channel 332 connecting the pump 315, so that the pump 315 communicates in alternation with one of the first and second reservoirs 303, 302, or with the outlet channel 313.

When the moving portion 311 is in a first lateral position in the stationary portion 310, the channel portion 342 of the moving portion 311 coincides with the channel 329 leading to the end-piece provided with the first orifice 307 of the first reservoir 303, so that the pump 315 is in fluid connection with the first reservoir 303. It can be understood that the other two channels 341, 343 are closed off in this first position.

When the moving portion 311 is in a second lateral position, the channel portion 341 of the moving portion 311 coincides with the channel 330 leading to the end-piece provided with the first orifice 307 of the second reservoir 302, so that the pump 315 is in fluid connection with the second reservoir 302. It can be understood that the other two channels 342, 343 are closed off in this second position.

Finally, when the moving portion 311 is in a third lateral position, the channel portion 343 of the moving portion 311 coincides with the outlet channel 313, so that the pump 315 is in fluid connection with the outlet for discharging the mixture. It can be understood that the other two channels 341, 342 are closed off in this third position.

Use of the mixing apparatus 301 of the invention is described below with reference to FIG. 7, it being understood that only the variations relative to the mixing apparatus 1 are described, the main steps being same as those described above for the mixing apparatus 1. The mixing apparatus 301 may be used to mix and to blend an ingredient in solid powder form or in lyophilized form contained in the second reservoir 302 with a solvent contained in the first reservoir 303, and then to discharge the mixture towards the outlet channel 313 and the needle 314.

As described above with reference to the mixing apparatus 1, the user fits the first, and second reservoirs 303, 302 over the end-pieces provided respectively with the first and second orifices 307, 306 in step 70, and then, in step 71, the user actuates the central monitoring and control unit 319 to trigger the mixing steps 72 to 76.

In step 72, the central monitoring and control unit 319 causes the moving portion 311 of the fluid-connection selector 309 to move laterally into the above-described first lateral position. Then, in the suction step 73, the central monitoring and control unit 319 actuates the pump 315 so as to suck the solvent contained in the first reservoir 303 into the pump 315.

Then, in step 74, the central monitoring and control unit 319 causes the moving portion 311 to move laterally into the above-described second lateral position. Thus, in the blending step 75, the pump 315 delivers the solvent into the second reservoir 302, and then the mixture is blended until it is fully homogenized by actuating the pump 315.

In a first operating mode, once the mixture is homogeneous, in step 76 the central monitoring and control unit 319 may cause the moving portion 311 to move laterally into the above-described third lateral position, with a view to administering the mixture directly via the outlet channel 313. In a second operating mode, it is also possible to store the resulting mixture in the second reservoir 302.

Figure 18:
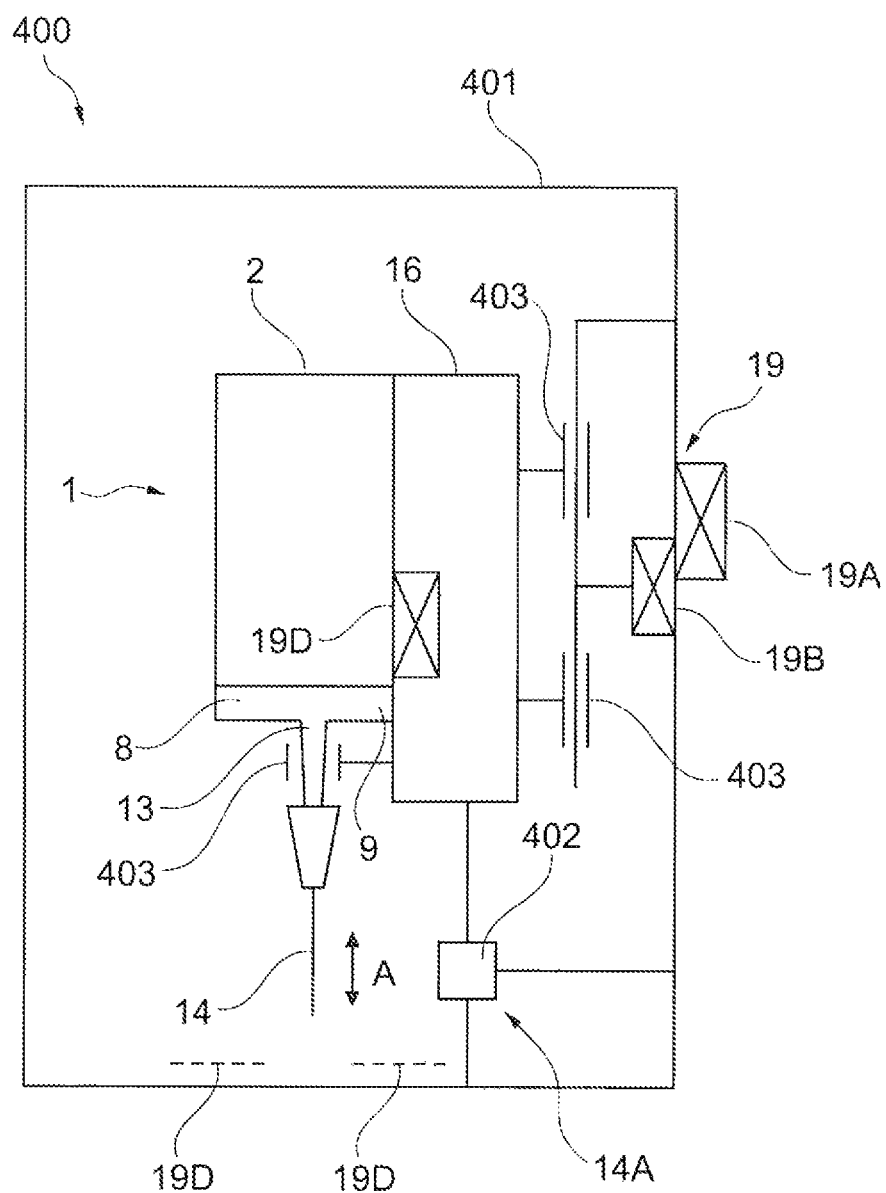
FIG. 18 is a diagrammatic view of injection apparatus of the invention including the mixing apparatus of the invention of FIG. 1.

FIG. 18 is a diagram showing medical-use miniaturized injection apparatus 400 including, in an enclosure 401, mixing apparatus 1 of the invention for homogeneously mixing ingredients of a mixture, and making it possible to inject said mixture into a patient via the injection needle 14.

FIG. 18 shows the second reservoir 2 of the mixing apparatus 1 mounted on the stand 8 and connected via the fluid-connection selector 9 of the outlet channel 13 leading to the injection needle 14. The stand 8 is connected to the frame 16 as described above with reference to FIGS. 1 to 3.

As shown in FIG. 18, the movement means 14A for moving the needle 14 comprise an actuator 402, e.g. in the form of a motor and of a rod-and-nut assembly or of a rack, or in the form of a set of springs, for moving the needle 14 relative to the enclosure 401 by using one or more guide means 403, e.g. slideways, for guiding the movement means 14A. More precisely, the assembly made up of the needle 14, of the stand 8, and of the frame 16 with all of the elements mounted on them is mounted to move relative to the enclosure 401 in the axial direction A.

It can be understood that, in order to improve the ergonomics of the injection apparatus 400, a portion of the central monitoring and control unit 19 may be mounted directly on the enclosure 401, said portion being, for example, the user interface 19A and/or the power supply 19B, as shown in FIG. 18.

In addition, a support (not shown) may be provided in the enclosure 401 for the purpose of supporting the second and first reservoirs 2, 3 so that the movement means 14A can also enable the second and first reservoirs 2, 3 to be perforated automatically, e.g. by the end-pieces provided with second and first orifices 6, 7, by means of the stand 8 being moved relative to the enclosure 401 in the axial direction A.

Thus, with a view to injecting a mixture of ingredients by using injection apparatus 400 of the invention, the user firstly mixes the ingredients by performing the steps 70 to 76 described above with reference to FIG. 7, and then, in step 77, the user actuates the movement means 14A for injecting the resulting mixture.

Thus, by means of the injection apparatus 400 of the invention, a single item of apparatus is obtained making it possible both to mix the ingredients of a mixture in simple, accurate, and automatic manner, and to administer the resulting mixture easily to a patient, without these operations requiring any particular training of the user. Naturally, the injection apparatus 400 may be fully adapted to receive mixing apparatus 101, or 201, or 301 of the invention as described above with reference respectively to FIGS. 8 and 9, to FIGS. 10 to 13, or to FIGS. 14 to 17.

Naturally, the present invention is in no way limited to the above description of the above-described embodiments, which can undergo modifications without going beyond the ambit of the invention.

Thus, in a variant, instead of being connected to the needle, the outlet channel may be connected to a cannula for a drip feed, to ambulatory apparatus, to some other bottle or container, or to any other means for administering the mixture.

In addition, the pump could be a pump having a diaphragm actuated by an electromagnet, or could be actuated by a piezoelectric device or by any other actuation means serving to transform any energy into mechanical energy.

In addition it is quite possible to provide a manual fluid-connection selector that is simple for the user to adjust.

In addition, the mixing apparatus 1, 101, 201, 301 of the invention is readily adaptable by adding one or more endpieces provided with orifices for other bottles or containers for other applications, and by adapting the fluid-connection selection accordingly. It is then also possible to provide an air intake in at least one channel of the selector in order to facilitate the operations of transferring volumes of fluid into or from small reservoirs.

In particular, the central monitoring and control unit may be adapted to trigger steps 76 and 77 adapted to various possibilities for administering the mixture: direct injection, oral route, temporary storage of the mixture with a view to subsequent administration, etc. For this purpose, the fluid-connection selector may be adapted to have a fluid-connection block position in order to avoid any leakage of the mixture.

For example, the mixture of ingredients may be stored in one of the reservoirs for subsequent administering, instead of discharging it towards the outlet channel. It is also possible to make provision to fill a series of small-size reservoirs from the mixing apparatus of the invention each with only a fraction of the mixture of ingredients, for administering to a plurality of patients, for example. This is particularly advantageous in a hospital context.

In addition, the central monitoring and control unit may advantageously be programmable so as to mix the ingredients at a chosen time, on the basis of a sequence and of parameters adapted to the ingredients and to the ambient conditions. For example, it is then advantageously possible to provide an alarm for indicating to the user that the mixture is ready.

In addition, the speed of the pump may advantageously be adjustable so as to adapt to the mixture of a variety of ingredients and in particular so as to avoid foaming or clumping. It is thus possible to provide vibratory apparatus, e.g. mechanical or ultrasound vibratory apparatus, or a turbulence mixer, interposed along one of the fluid-connection channels, or indeed a filter mounted on the pump, in order to prevent clumping.

Finally, the mixing apparatus may include a plurality of pumps and/or a plurality of fluid-connection selectors, it being possible for each pump and for each selector to be dedicated to a specific mixture.

The invention makes it possible to achieve the above-mentioned objectives while also offering major advantages.

Firstly, when the mixing apparatus 1, 101, 201, 301 of the invention administers the mixture directly, e.g. using the injection apparatus 400 of the invention, a single pump is used very advantageously for mixing, for blending, and for administering a substance obtained by mixing two or more ingredients.

In addition, at the time of administering of the mixture, all of the fluid-connection circuits and the pump are primed with a homogeneous mixture enabling the active ingredient to be metered extremely accurately in the apparatus of the invention, while limiting the negative impact of the dead volume of known apparatus.

The invention claimed is:

1. A mixing apparatus for mixing a first ingredient and a second ingredient coming respectively from a first reservoir and a single second reservoir distinct from said first reservoir, said mixing apparatus comprising a first orifice suitable for being connected to said first reservoir, and two second orifices distinct from said first orifice and suitable for being connected to said single second reservoir, a motor-driven fluid-connection selector including a stationary portion with channels opening out via said first orifice and via said second orifices and a moving portion including a moving channel moving relative to said stationary portion between a plurality of positions to selectively put said first orifice and said second orifices into communication with a motor-driven pump having a first port and a second port coupled through the pump, and a central monitoring and control unit actuated for driving said motor-driven fluid-connection selector and said motor-driven pump among a plurality of operation modes including:
a first operation mode in which said central monitoring and control unit causes said moving portion of said fluid-connection selector to move so as to put in communication said first orifice and at least one of said second orifices with said first port and said second port of said pump, in which said central monitoring and control unit actuates said pump to transfer said first ingredient from said first reservoir to said second reservoir through said moving channel and said pump to make a mixture with said first and said second ingredients,
a second operation mode in which said central monitoring and control unit causes said moving portion of said fluid-connection selector to move so as to put in communication said two second orifices with said two ports of said pump and then to actuate said pump to flow said mixture through said pump and said two second orifices so as to blend said mixture of the first ingredient and the second ingredient into a homogenous mixture.

2. The mixing apparatus according to claim 1, wherein said channels of said fluid-connection selector includes at least one outlet channel for discharging said mixture from said mixing apparatus, wherein said fluid-connection selector is switchable into a third operation mode in which said moving portion puts said pump or at least one of said second orifices into communication with said outlet channel in order to discharge said mixture from said mixing apparatus.

3. The mixing apparatus according to claim 1, wherein said first orifice is formed individually on an end-piece.

4. The mixing apparatus according to claim 1, wherein said two second orifices have mutually different inside end section dimensions, so as to improve the flow of fluid through said second reservoir.

5. The mixing apparatus according to claim 1, wherein said mixing apparatus includes a disposable first assembly and a reusable second assembly arranged to be connectable and detachable respectively one relative to the other, said reusable second assembly including motor drives of said motor-driven fluid-connection selector and said motor-driven pump.

6. The mixing apparatus according to claim 5, wherein said disposable first assembly includes said first reservoir and said second reservoir.

7. The mixing apparatus according to claim 1, wherein said moving portion of said fluid-connection selector is arranged to be movable in rotation relative to said stationary portion.

8. A medical-use miniaturized injection apparatus comprising a mixing apparatus according to claim 1, and a needle connected to said fluid-connection selector.

9. The injection apparatus according to claim 8, wherein said needle is an injection needle connected to an outlet channel of said fluid-connection selector and mounted to move in an enclosure of said injection apparatus and being able to project out of said enclosure in order to discharge said mixture from said mixing apparatus such as to inject said mixture into a patient.

10. The mixing apparatus according to claim 1, wherein the two second orifices suitable for being coupled to said second reservoir have different lengths, so as to improve the flow of fluid through said second reservoir.

11. The mixing apparatus according to claim 1, wherein said first reservoir contains a solvent and said second reservoir containing a solid powder or a lyophilized substance.

* * * * *